(12) United States Patent
Hirano et al.

(10) Patent No.: US 8,110,381 B2
(45) Date of Patent: Feb. 7, 2012

(54) L-GLUTAMIC ACID-PRODUCING BACTERIUM AND METHOD FOR PRODUCTION OF L-GLUTAMIC ACID

(75) Inventors: Seiko Hirano, Kawasaki (JP); Jun Nakamura, Kawasaki (JP); Hisao Ito, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 935 days.

(21) Appl. No.: 12/034,087

(22) Filed: Feb. 20, 2008

(65) Prior Publication Data

US 2010/0279363 A1    Nov. 4, 2010

Related U.S. Application Data

(63) Continuation of application No. PCT/JP2006/317037, filed on Aug. 23, 2006.

(30) Foreign Application Priority Data

Aug. 26, 2005  (JP) ................................ 2005-245213

(51) Int. Cl.
*C12P 13/14* (2006.01)
(52) U.S. Cl. ...................................................... 435/110
(58) Field of Classification Search ........................ None
See application file for complete search history.

(56) References Cited

U.S. PATENT DOCUMENTS

| | | | |
|---|---|---|---|
| 5,977,331 A | 11/1999 | Asakura et al. | |
| 6,962,989 B1 * | 11/2005 | Pompejus et al. | 536/23.7 |
| 7,097,999 B2 | 8/2006 | Tsujimoto et al. | |
| 7,205,132 B2 | 4/2007 | Hirano et al. | |
| 7,211,416 B2 | 5/2007 | Asahara et al. | |
| 7,300,776 B2 | 11/2007 | Ito et al. | |
| 7,335,496 B2 | 2/2008 | Yamamoto et al. | |
| 2002/0160461 A1 | 10/2002 | Nakai et al. | |
| 2004/0002143 A1 | 1/2004 | Asakura et al. | |
| 2004/0152175 A1 | 8/2004 | Nakamura et al. | |
| 2005/0196846 A1 | 9/2005 | Hara et al. | |
| 2005/0277179 A1 | 12/2005 | Takai et al. | |
| 2006/0141588 A1 | 6/2006 | Nakamura et al. | |
| 2006/0160191 A1 | 7/2006 | Kataoka et al. | |
| 2006/0205043 A1 | 9/2006 | Tsujimoto et al. | |
| 2006/0216796 A1 | 9/2006 | Hashiguchi et al. | |
| 2007/0172932 A1 | 7/2007 | Hirano et al. | |
| 2007/0254345 A1 | 11/2007 | Fukui et al. | |

FOREIGN PATENT DOCUMENTS

| | | |
|---|---|---|
| CN | 1335394 | 2/2002 |
| DE | 101 28 510 | 12/2002 |
| EP | 1 002 866 | 5/2000 |
| EP | 1 174 508 | 1/2002 |
| JP | 1-296994 | 11/1989 |

OTHER PUBLICATIONS

First Office Action from Chinese Patent App. No. 200680031157.4 (Dec. 25, 2009) with English translation thereof.
Ikeda, M., et al., "The *Corynebacterium glutamicum* genome: features and impacts on biotechnological processes," Appl. Microbiol. Biotechnol. 2003;62:99-109.
International Preliminary Examination Report on Patentability and Written Opinion of the International Searching Authority for PCT Patent App. No. PCT/JP2006/317037 (Aug. 21, 2008).
Kimura, E., et al., "Glutamate Overproduction in *Corynebacterium glutamicum* Triggered by a Decrease in the Level of a Complex Comprising DtsR and a Biotin-containing Subunit," Biosci. Biotechnol. Biochem. 1999;63(7):1274-1278.
Supplementary European Search Report for EP Patent App. No. 06797012.9 (Jun. 5, 2009).
Database DDBJ/EMBL/GenBank [on line] Kalinowski et al., Definition: hypothetical protein predicted by Glimmer/Critica *Corynebacterium glutamicum* ATCC 13032, 1 pg., Accession No. CAF20999, 2006.
Kalinowski, J., et al., "The complete *Corynebacterium glutamicum* ATCC 13032 genome sequence and its impact on the production of L-aspartate-derived amino acids and vitamins," J. Biotechnol. 2003;104:5-25.
Nishiyama, T., "The Transition of Research on Industrial Microorganism for L-glutamate Overproduction Using *Coryneform* Bacteria," Sci. Technol. 2000;19(75):18-21.
Schäfer, A., et al., "Small mobilizable multi-purpose cloning vectors derived from the *Escherichia coli* plasmids pK18 and pK19: selection of defined deletions in the chromosome of *Corynebacterium glutamicum*," Gene 1994;145:69-73.
U.S. Appl. No. 60/641,079, Nakamura et al., filed Jan. 4, 2005.
U.S. Appl. No. 60/641,080, Nakamura et al., filed Jan. 4, 2005.
U.S. Appl. No. 60/644,040, Kataoka et al., filed Jan. 18, 2005.
U.S. Appl. No. 60/651,229, Hirano et al., filed Feb. 10, 2005.
U.S. Appl. No. 60/673,338, Kataoka et al., filed Apr. 21, 2005.
U.S. Appl. No. 60/715,131, Nakamura et al., filed Sep. 9, 2005.
U.S. Appl. No. 60/651,229, Hirano et al., filed Nov. 10, 2005.
U.S. Appl. No. 11/844,559, Hara et al., filed Aug. 25, 2007.

* cited by examiner

*Primary Examiner* — Rebecca E. Prouty
(74) *Attorney, Agent, or Firm* — Shelly Guest Cermak; Cermak Nakajima LLP

(57) ABSTRACT

A method for producing L-glutamic acid by culturing a coryneform bacterium in which the gluX is inactivated in a medium to produce L-glutamic acid in the medium or cells, and collecting L-glutamic acid from the medium.

3 Claims, 3 Drawing Sheets

L-GLUTAMIC ACID-PRODUCING BACTERIUM AND METHOD FOR PRODUCTION OF L-GLUTAMIC ACID

This application is a continuation of PCT/JP2006/317037, filed Aug. 23, 2006. This application also claims priority under 35 U.S.C. §119 to Japanese application 2005-245213 filed on Aug. 26, 2005. Each of these documents is incorporated in their entireties by reference. The Sequence Listing in electronic format filed herewith is also hereby incorporated by reference in its entirety (File Name: US-356_Seq_List_Copy_1; File Size: 19 KB; Date Created: Feb. 20, 2008).

BACKGROUND OF THE INVENTION

1. Field of the Invention

The present invention relates to the fermentation industry, and more specifically relates to a method for efficiently producing L-glutamic acid using a coryneform bacterium.

2. Brief Description of the Related Art

L-glutamic acid is conventionally produced by fermentation using coryneform bacteria belonging to the genus *Brevibacterium*, *Corynebacterium*, or the like, which are able to produce L-glutamic acid. In order to improve productivity of these coryneform bacteria, strains isolated from nature, mutant strains, or strains modified by gene recombination are typically used.

To improve the production of L-glutamic acid by coryneform bacteria using gene recombination techniques, it has been reported that the activities of glutamate dehydrogenase, citrate synthase, and pyruvate carboxylase may be enhanced (International Patent Publication WO00/18935), or the activities of α-ketoglutarate dehydrogenase, or α-ketoglutarate dehydrogenase, and isocitrate lyase may be reduced (International Patent Publication WO95/34672 and Japanese Patent Laid-open (KOKAI, JP-A) No. 01-296994), and so forth.

The entire nucleotide sequence of the *Corynebacterium glutamicum* chromosome has been determined (Appl. Microbiol. Biotechnol., 62 (2-3), pp. 99-109 (2003)). However, about 40% of the 3099 putative orfs in this chromosome exhibit low homology to the corresponding genes of other microorganisms with known functions, and therefore encode proteins with unknown functions. Consequently, the effect of deleting these putative orfs has not been reported.

SUMMARY OF THE INVENTION

An aspect of the present invention is to provide a coryneform bacterium with improved L-glutamic acid producing ability, and to provide a method for efficiently producing L-glutamic acid using such a bacterium.

The inventors of the present invention conducted research in order to achieve the aforementioned aspect. As a result, it was found that if the gluX gene was inactivated in coryneform bacteria, the L-glutamic acid producing ability of the bacteria was improved.

That is, the present invention provides the following:

It is an aspect of the present invention to provide an isolated coryneform bacterium which is able to produce L-glutamic acid, wherein the gluX gene is inactive in said bacterium.

It is a further aspect of the present invention to provide the coryneform bacterium as described above, wherein expression of the gluX gene is decreased by introducing a mutation into the gluX gene or an expression control region thereof on the chromosome of the bacterium.

It is a further aspect of the present invention to provide the coryneform bacterium as described above, wherein the gluX gene on the chromosome is disrupted.

It is a further aspect of the present invention to provide a method for producing L-glutamic acid comprising
A) culturing a coryneform bacterium as described above in a medium, and
B) collecting L-glutamic acid from the medium.

DESCRIPTION OF THE PREFERRED EMBODIMENTS

Figure 1:
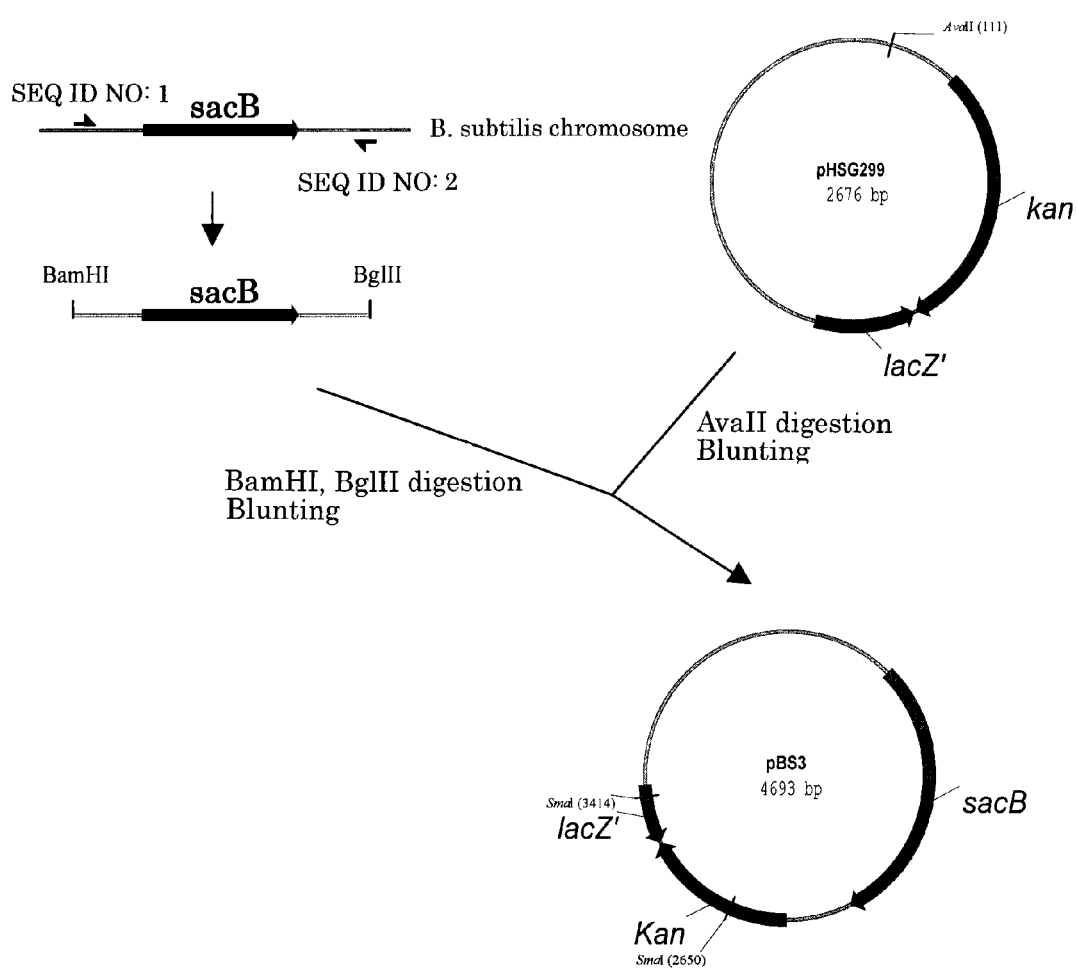
FIG. 1 shows the construction of the plasmid pBS3.

Hereafter, embodiments of the present invention will be explained in detail.
<1> Coryneform Bacterium of the Present Invention The coryneform bacteria include *Corynebacterium* bacteria and those bacteria which had been previously classified into the genus *Brevibacterium*, but have been re-classified into the genus *Corynebacterium* (Int. J. Syst. Bacteriol., 41, 255 (1981)), and further include bacteria belonging to the genus *Brevibacterium*, which is extremely close to the genus *Corynebacterium*. Specific examples include the following:
  *Corynebacterium acetoacidophilum*
  *Corynebacterium acetoglutamicum*
  *Corynebacterium alkanolyticum*
  *Corynebacterium callunae*
  *Corynebacterium glutamicum*
  *Corynebacterium lilium*
  *Corynebacterium melassecola*
  *Corynebacterium thermoaminogenes* (*Corynebacterium efficiens*)
  *Corynebacterium herculis*
  *Brevibacterium divaricatum*
  *Brevibacterium flavum*
  *Brevibacterium immariophilum*
  *Brevibacterium lactofermentum* (*Corynebacterium glutamicum*)
  *Brevibacterium roseum*
  *Brevibacterium saccharolyticum*
  *Brevibacterium thiogenitalis*
  *Brevibacterium ammoniagenes*
  *Brevibacterium album*
  *Brevibacterium cerinum*
  *Microbacterium ammoniaphilum*
  Specifically, the following strains can be mentioned:
  *Corynebacterium acetoacidophilum* ATCC 13870
  *Corynebacterium acetoglutamicum* ATCC 15806
  *Corynebacterium alkanolyticum* ATCC 21511
  *Corynebacterium callunae* ATCC 15991
  *Corynebacterium glutamicum* ATCC 13020, ATCC 13032, ATCC 13060, ATCC 13869
  *Corynebacterium lilium* ATCC 15990
  *Corynebacterium melassecola* ATCC 17965
  *Corynebacterium thermoaminogenes* AJ12340 (FERM BP-1539)
  *Corynebacterium herculis* ATCC 13868
  *Brevibacterium divaricatum* ATCC 14020
  *Brevibacterium flavum* ATCC 13826, ATCC 14067, AJ12418 (FERM BP-2205)
  *Brevibacterium immariophilum* ATCC 14068

*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from the American Type Culture Collection, and may be obtained by their designated registration number. The registration number corresponding to each strain is listed in the catalogue of the ATCC. The AJ12340 strain was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Oct. 27, 1987 under the provisions of the Budapest Treaty and given an accession number of FERM BP-1539. The AJ12418 strain was deposited at National Institute of Bioscience and Human Technology, Agency of Industrial Science and Technology, Ministry of International Trade and Industry on Jan. 5, 1989 under the provisions of the Budapest Treaty and given an accession number of FERM BP-2205.

In the present invention, "L-glutamic acid producing ability" or "able to produce L-glutamic acid" means that the bacteria have an ability to produce L-glutamic acid in a medium when they are cultured in the medium. The bacteria may inherently have the ability to produce L-glutamic acid, or the ability may be imparted by breeding. Furthermore, the L-glutamic acid producing ability may be imparted by modifying the bacterium so that the gluX is inactivated in the manner described herein.

Conventional methods which have been used to breed coryneform bacteria may be used to impart the ability to produce L-glutamic acid. For example, methods may be used to acquire metabolic regulation mutant strains, or methods whereby a recombinant strain is constructed in which an enzyme of a biosynthesis system of an objective substance is enhanced (refer to "Amino Acid Fermentation", the Japan Scientific Societies Press [Gakkai Shuppan Center], 1st Edition, published on May 30, 1986, pp. 77-100), and so forth. These methods may performed individually, or in combination.

Hereinafter, methods for imparting L-glutamic acid producing ability are described. For example, the expression of a gene encoding an enzyme involved in L-glutamic acid biosynthesis may be enhanced or increased. Examples of such enzymes include glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, glucose phosphate isomerase, and so forth.

Expression may be increased or enhanced by constructing a plasmid which contains a DNA fragment containing any of these genes, and at least a gene responsible for replication of the plasmid, and introducing this plasmid into the coryneform bacteria. Other methods of increasing gene expression include increasing the copy number of these genes on the bacterial chromosome by conjugation, gene transfer, etc., introducing a mutation into the promoter region of these genes, or replacing the native promoter with a stronger promoter (refer to International Patent Publication WO00/18935).

When a gene is amplified in a plasmid or on the chromosome, any promoter, including the native promoter for the gene being amplified, may be used as long as it functions in the chosen coryneform bacteria. The amount of gene expression can be controlled by choosing a suitable promoter. Examples of coryneform bacteria which have been modified to enhance expression of the citrate synthase gene, phosphoenolpyruvate carboxylase gene, glutamate dehydrogenase gene, and/or isocitrate dehydrogenase gene are described in International Patent Publication WO00/18935 and European Patent Publication No. 1010755.

Moreover, the L-glutamic acid producing ability may also be attained by reducing or deleting the activity of an enzyme that catalyzes a reaction which directs a diversion from the biosynthetic pathway of L-glutamic acid. Such diversions result in other compounds being produced instead of L-glutamic acid. Examples of enzymes that catalyze reactions resulting in the synthesis of a compound other than L-glutamic acid include isocitrate lyase, α-ketoglutarate dehydrogenase, acetyl phosphate transferase, acetate kinase, acetohydroxy acid synthase, acetolactate synthase, acetyl formate transferase, lactate dehydrogenase, glutamate decarboxylase, 1-pyrroline dehydrogenase, and so forth.

In order to reduce or delete the activity of any of the enzymes described above, a mutation can be introduced into the gene which encodes the enzyme on the chromosome by a known mutagenesis method. For example, the gene encoding the enzyme on the chromosome can be deleted, or an expression control sequence such as the promoter, Shine-Dalgarno (SD) sequence, operator, terminator and/or attenuator can be modified by gene recombination. In addition, a mutation resulting in an amino acid substitution (missense mutation), a stop codon (nonsense mutation), or a frame shift mutation that adds or deletes one or two nucleotides to the region encoding the enzyme on the chromosome may be introduced, or the gene can be partially or entirely deleted (Journal of Biological Chemistry, 272:8611-8617 (1997)). Furthermore, enzymatic activity can also be reduced or deleted by deleting the coding region of the objective gene in a DNA construct, and replacing the normal gene on the chromosome by homologous recombination or the like with the DNA construct. Examples of coryneform bacteria which have reduced α-ketoglutarate dehydrogenase activity include the following strains (described in Japanese Patent Laid-open Nos. 07-834672, 06-237779, 01-296994, etc.):

*Brevibacterium lactofermentum* ΔS strain (WO95/34672)
*Brevibacterium lactofermentum* AJ12821 strain (FERM BP-4172; see FR9401748)
*Brevibacterium flavum* AJ12822 strain (FERM BP-4173; see FR9401748)
*Corynebacterium glutamicum* AJ12823 strain (FERM BP-4174; see FR9401748)

Other methods of imparting L-glutamic acid producing ability include imparting resistance to organic acid analogs or respiratory inhibitors, or imparting sensitivity to inhibitors of cell wall synthesis. Examples of such methods include, for example, imparting resistance to benzopirone or naphtoquinones (JP56-1889A), imparting resistance to HOQNO (JP56-140895A), imparting resistance to α-ketomalonic acid (JP57-2689A), imparting resistance to guanidine (JP56-35981A), imparting sensitivity to penicillin (JP04-88994A), and the like.

Specific examples of such bacteria include the following strains:

*Brevibacterium flavum* AJ11355 (FERM P-5007; JP56-1889A)

*Corynebacterium glutamicum* AJ11368 (FERM P-5020; JP56-1889A)

*Brevibacterium flavum* AJ11217 (FERM P-4318; JP57-2689A)

*Corynebacterium glutamicum* AJ11218 (FERM P-4319; JP57-2689A)

*Brevibacterium flavum* AJ11564 (FERM P-5472; JP56-140895A)

*Brevibacterium flavum* AJ11439 (FERM P-5136; JP56-35981A)

*Corynebacterium glutamicum* H7684 (FERM BP-3004; JP04-88994A)

The parent strain used to derive the coryneform bacterium of the present invention may also be able to produce L-glutamic acid under favorable conditions for production of L-glutamic acid, such as restricting biotin, adding surfactant, and/or penicillin (referred to as "L-glutamic acid producing conditions"). "L-glutamic acid producing conditions" indicates when a substance that induces L-glutamic acid production is added to a medium containing a carbon source, a nitrogen source, inorganic salts, and a trace amount of organic nutrients, such as amino acids and vitamins, if necessary. Also, such conditions can indicate that substances that inhibit L-glutamic acid production are limited in the medium. Substances that induce L-glutamic acid production include antibiotics such as penicillin G and surfactants including saturated fatty acids, such as Tween 40, 60, or the like. Biotin is an example of a substance that inhibits L-glutamic acid production (Amino Acid Fermentation, Japan Scientific Societies Press 1986).

The concentration of these substances in the medium are as follows. The concentration of biotin is less than 30 μg/L, preferably less than 20 μg/L, more preferably less than 10 μg/L, and the medium may not contain biotin at all. The concentration of penicillin in the medium is not less than 0.1 U/ml, preferably not less than 0.2 U/ml, more preferably not less than 0.4 U/ml. The concentration of surfactant in the medium is not less than 0.5 g/L, preferably not less than 1 g/L, more preferably not less than 2 g/L. However, any concentration of these substances may be used as long as L-glutamic acid production is induced. In addition, when a medium contains an antibiotic or surfactant, the medium should contain a high concentration of biotin. In such a case, it is preferable that the medium contains more than 50 μg/L, preferably more than 100 μg/L, more preferably more than 200 μg/L, of biotin.

Examples of the parent strain include wild-type strains of coryneform bacteria as described above, and the following strains:

*Brevibacterium flavum* AJ11217 (FERM P-4318; JP57-2689A)

*Corynebacterium glutamicum* AJ11218 (FERM P-4319; JP57-2689A)

*Brevibacterium lactofermentum* AJ11426 (FERM P-5123 JP56-048890A)

*Corynebacterium glutamicum* AJ11440☐FERM P-5137 JP56-048890A☐

*Brevibacterium lactofermentum* AJ11796 (FERM P-6402 JP58-158192A)

The L-glutamic acid producing coryneform bacterium of the present invention is modified so that the gluX gene is inactivated. The coryneform bacterium can be obtained by modifying a coryneform bacterium having L-glutamic acid producing ability so that the gluX gene is inactivated. When breeding the coryneform bacterium, either the L-glutamic acid producing ability can be imparted first, or the gluX gene may be inactivated first.

The expression "modified so that the gluX gene is inactivated" indicates that the number of molecules of the GluX protein encoded by the gluX gene per cell is decreased when compared to that of the parent strain, a wild-type strain, or an unmodified strain, or indicates that the activity of the GluX protein per molecule is decreased, or indicates that the GluX protein molecule is no longer produced, and so forth. For example, this expression indicates that the amount of the protein encoded by the gluX gene is decreased as compared to that of a non-modified strain or a wild-type strain, that the expression amount of the gluX gene is decreased, that the three-dimensional conformation of the protein is modified and thus the normal GluX protein cannot be produced, or that the GluX protein is not produced at all. The wild-type coryneform bacterium used as the reference for comparison is, for example, *Corynebacterium glutamicum* (*Brevibacterium lactofermentum*) ATCC 13869 or ATCC 13032.

A reduction of expression of the gluX gene can be confirmed by comparing the amount of the gluX mRNA in the modified strain with that in a wild-type or non-modified strain. Methods for confirming expression include Northern hybridization and RT-PCR (Molecular Cloning, Cold Spring Harbor Laboratory Press, Cold Spring Harbor (USA) 2001). The degree to which expression is reduced is not particularly limited so long as expression is reduced as compared to that of a wild-type strain or non-modified strain. However, expression is desirably reduced, for example, by at least 75%, 50%, 25%, 10%, or less as compared to a wild-type strain or non-modified strain, or the expression may be completely eliminated.

A reduction in the amount of the protein encoded by the gluX gene can be confirmed by detection via Western blotting using antibodies (Molecular Cloning, Cold Spring Harbor Laboratory Press, Cold Spring Harbor (USA), 2001). The degree to which the amount of produced protein is reduced is not particularly limited so long as it is reduced as compared to that of a wild-type strain or non-modified strain. However, it is desirably reduced, for example, by at least 75%, 50%, 25%, 10%, or less as compared to a wild-type strain or non-modified strain, or the activity may be completely eliminated, which means that the protein is not produced at all.

The protein encoded by the gluX gene—the GluX protein—functions to improve the production of L-glutamic acid through inactivation of the gluX gene on the chromosome. The GluX protein which is native to coryneform bacteria includes the amino acid sequence shown in SEQ ID NO: 17, and is encoded by the gluX gene of *Corynebacterium glutamicum* (*Brevibacterium lactofermentum*) ATCC 13869 or *Corynebacterium glutamicum* ATCC 13032 (nucleotide numbers 1001 to 1279 of SEQ ID NO: 16). The gluX gene of *Corynebacterium glutamicum* ATCC 13032 is encoded by the nucleotides 2475838 to 2476119 in the genome sequence registered as Genbank Accession No. NC_003450, and is registered as NCgl2252. Moreover, since the nucleotide sequence of the gluX gene may differ depending on species or strains of coryneform bacteria, the nucleotide sequence of the gluX gene may vary from the nucleotide numbers 1001 to 1279 of SEQ ID NO: 16. Such variants can be determined by searching for close matches to the nucleotide sequence of numbers 1001 to 1279 of SEQ ID NO: 16 using BLAST or the like (http://blast.genome.jp/). Moreover, variants of the gluX gene include gluX gene homologues, for example, genes that can be amplified by PCR using the chromosome of a coryneform bacterium as a template and synthetic oligonucleotides of SEQ ID NOS: 13 and 14 as primers.

Examples of the GluX protein include proteins having the amino acid sequence of SEQ ID NO: 17. However, since the exact protein sequence may differ depending on the species or strain of the coryneform bacteria, and the nucleotide sequence of the gene encoding GluX may differ, gluX may encode amino acid sequences as described above but which include one or more amino acid changes, such as substitutions, deletions, insertions, or additions, as long as the function of the GluX protein does not change. The number of possible amino acid changes is, for example, 1 to 20, preferably 1 to 10, more preferably 1 to 5. The amino acid changes are conservative mutations that allow for normal production of the GluX protein. Conservative substitutions include: substitutions of the aromatic amino acids Phe, Trp, and Tyr for each other, substitutions of the hydrophobic amino acids Leu, Ile, and Val for each other, substitutions of the polar amino acids Gln and Asn for each other, substitutions of the basic amino acids Arg, Lys, and His for each other, substitutions of the acidic amino acids Asp and Glu for each other, and substitutions of the hydroxyl group-containing amino acids Ser and Thr for each other. Typical conservative mutations are conservative substitutions, which include: substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of zGly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr and substitution of Met, Ile, or Leu for Val.

A variant of the gluX gene may also be a DNA which is able to hybridize with the nucleotide sequence of 1001 to 1279 of SEQ ID NO: 16, or a probe that can be prepared from the nucleotide sequence under stringent conditions. The "stringent conditions" are conditions under which a so-called specific hybrid is formed, and a non-specific hybrid is not formed. Examples of the stringent conditions include those under which highly homologous DNAs hybridize to each other, for example, DNAs not less than 80, 90, 95, or 97% homologous, hybridize to each other, and DNAs less homologous than the above do not hybridize to each other, or washing once or preferably 2 or 3 times at a salt concentration and temperature typical for washing for Southern hybridization, i.e., 1×SSC, 0.1% SDS at 60° C., preferably 0.1×SSC, 0.1% SDS at 60° C., more preferably 0.1×SSC, 0.1% SDS at 68° C. The length of the probe may be appropriately selected depending on the hybridization conditions. But, the length is typically 100 bps to 1 kbps.

The expression "modified so that the gluX gene is inactivated" means that the GluX protein encoded by the inactivated gluX gene does not function normally. Bacteria modified in such a manner can be obtained by introducing a mutation to the GluX protein using a reagent or the like so that the protein does not function normally, or introducing a mutation into the gluX gene by gene engineering techniques or the like so that the amount of the GluX protein is decreased or the bacterium no longer produces the GluX protein, or the like.

This may be achieved by, for example, deleting the gluX gene on the chromosome, or by modifying an expression control sequence such as a promoter, Shine Dargarno (SD) sequence, or the like. In addition, an amino acid substitution (missense mutation), a stop codon (nonsense mutation), or a frame shift mutation which adds or deletes one or two nucleotides into a coding region may be introduced, or a portion, or the entire gene, may be deleted (Journal of Biological Chemistry 272:8611-8617 (1997), Proceedings of the National Academy of Sciences, USA 95 5511-5515 (1998), Journal of Biological Chemistry 266, 20833-20839 (1991)).

If inactivating the gluX gene by deleting a portion of the gene, either a region on the N-terminus side or a region on the C-terminus side may be deleted so long as a non-functioning GluX protein is produced. Furthermore, inactivation of the gluX gene can also be attained by introducing a transposon carrying an antibiotic resistance gene or a gene useful for L-glutamic acid production into the coding region of gluX.

Introduction of such mutations as described above into the gluX gene can be attained by, for example, preparing a deletion-type gene (the gluX gene with a portion deleted) which does not produce the functioning GluX protein, and transforming a coryneform bacterium with a DNA containing the deletion-type gene to induce homologous recombination of the deletion-type gene and the gluX gene on the chromosome. These techniques have been established, and examples include using a linear DNA called "Red-driven integration" developed by Datsenko and Wanner (Proc. Natl. Acad. Sci. USA, 2000, Vol. 97, No. 12, pp. 6640-6645), using a plasmid containing a temperature-sensitive replication origin (U.S. Pat. No. 6,303,383, Japanese Patent Laid-open No. 05-007491), and so forth. Moreover, such techniques as described above can also be performed using a plasmid which is unable to replicate in the host, or a plasmid which is capable of conjugative transfer to coryneform bacteria.

Examples temperature-sensitive plasmids for coryneform bacteria include p48K and pSFKT2 (see Japanese Patent Laid-open No. 2000-262288 for these), pHSC4 (see French Patent Laid-open No. 2667875, 1992 and Japanese Patent Laid-open No. 5-7491), and so forth. These plasmids can autonomously replicate at a minimum of 25° C., but cannot autonomously replicate at 37° C. in coryneform bacteria. The *Escherichia coli* AJ12571 harboring pHSC4 was deposited at the National Institute of Bioscience and Human-Technology, the Agency of Industrial Science and Technology, the Ministry of International Trade and Industry (currently, the independent administrative corporation, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-5466)) on Oct. 11, 1990, receiving an accession number of FERM P-11763. Then, the deposit was converted into an international deposit under the provisions of the Budapest Treaty on Aug. 26, 1991, receiving an accession number of FERM BP-3524.

A plasmid which is replicable in *Escherichia coli* is preferred as a plasmid which cannot replicate in coryneform bacteria, and examples include pHSG299 (Takara Bio Inc.), pHSG399 (Takara Bio Inc.), and so forth. An example of a plasmid capable of conjugative transfer is pK19mobsacB (J. Bacteriology, 174:5462-65 (1992)). The deletion-type gene which does not produce the GluX protein includes the gene in which the entire or a partial region of SEQ ID NO: 16 is deleted, the gene with a missense mutation, the gene with a transposon or a marker gene inserted therein, the gene with a nonsense mutation, and the gene with a frameshift mutation, but the examples are not limited to these.

The inactivation of the gluX gene may be performed by the following methods. The deletion-type gene of the gluX gene can be obtained by the following methods. The gluX gene can be obtained by preparing chromosomal DNA from a coryneform bacterium by the method of Saito and Miura (refer to H. Saito and K. Miura, Biochem. Biophys. Acta, 72, 619 (1963); Text for Bioengineering Experiments, Edited by the Society for Bioscience and Bioengineering, Japan, pp. 97-98, Baifukan, 1992), and performing PCR using oligonucleotides constructed based on the sequences from a database such as Genbank, and the gene can be cloned using the synthetic oligonucleotides of SEQ ID NOS: 13 and 14. The deletion-type gene can be obtained by amplifying the full length gluX gene by PCR, and digesting the PCR product with a restriction enzyme which cleaves at an internal site, or by amplifying a part of the coding region of the gluX gene by PCR.

Then, the deletion-type gene is introduced into a plasmid which is temperature-sensitive in coryneform bacteria, or a plasmid which cannot replicate in coryneform bacteria, and the coryneform bacterium is transformed with the recombinant plasmid. Transformation may be performed according to a known method, such as by treating recipient cells with calcium chloride so as to increase permeability for the DNA, which has been reported for *Escherichia coli* K-12 (Mandel, M. and Higa, A., J. Mol. Biol., 53, 159 (1970)), and by preparing competent cells from cells which are at the growth phase, followed by transformation with DNA, which has been reported for *Bacillus subtilis* (Duncan, C. H., Wilson, G. A. and Young, F. E., Gene, 1, 153 (1977)). Alternatively, recombinant DNA may be introduced into recipient cells, which has been reported for *Bacillus subtilis*, actinomycetes, and yeasts (Chang, S, and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)). In addition, coryneform bacteria can also be transformed by the electric pulse method (JP2-207791A). When a plasmid which does not replicate in coryneform bacteria is used in the transformation, the gluX gene on the plasmid and the gluX gene on a chromosome are recombined in the transformant. When a temperature-sensitive plasmid is used, the transformant is cultured at a temperature at which the replication origin does not function (25° C.) to obtain a strain containing the plasmid. The strain containing the plasmid is cultured at a high temperature to eliminate the temperature-sensitive plasmid, and then applied to a plate containing an antibiotic. Since the temperature-sensitive plasmid cannot proliferate at the high temperature, the strain cannot grow on the plate containing an antibiotic, but the strain in which the gluX gene on the plasmid and the gluX gene on a chromosome have recombined will grow and appear on the plate, although at an extremely low frequency.

In the strain containing the recombinant DNA on the bacterial chromosome as described above, recombination with the native gluX gene results, and thus two fusion genes, the chromosomal gluX gene and the deletion-type gluX gene, and the remaining portion of the recombinant DNA (vector portion, temperature-sensitive replication origin, and drug-resistance marker), which is located between the fusion genes, are inserted into the chromosome.

Then, in order to leave only the deletion-type gluX gene on the chromosomal DNA, the gluX gene is eliminated with the vector portion (including the temperature-sensitive replication origin and drug-resistance marker) from the chromosomal DNA. Then, either the native gluX gene is left on the chromosomal DNA, and the deletion-type gluX gene is excised, or to the contrary, the deletion-type gluX gene is left on the chromosomal DNA, and the native gluX gene is excised. The strain containing the deletion-type gluX gene on the chromosome can be selected by PCR or Southern hybridization.

Furthermore, the sacB gene encoding levansucrase, expression of which is fatal to coryneform bacteria, may also be used as a marker of homologous recombination (Schafer, A. et al., Gene, 145, pp. 69-73 (1994)). That is, if levansucrase is expressed in coryneform bacteria, levan produced by assimilation of sucrose will prevent growth of the bacteria. Therefore, if a vector encoding levansucrase remains on the bacterial chromosome, and the bacteria is cultured on a plate containing sucrose, the strain cannot grow, and thus only a strain in which the vector is eliminated can be selected on a plate containing sucrose.

As the sacB gene or homologous gene thereof, the following sequences can be used:

*Bacillus subtilis*: sacB GenBank Accession Number X02730 (SEQ ID NO: 7)

*Bacillus amyloliquefaciens*: sacB GenBank Accession Number X52988

*Zymomonas mobilis*: sacB GenBank Accession Number L33402

*Bacillus stearothermophilus*: surB GenBank Accession Number U34874

*Lactobacillus sanfranciscensis*: frfA GenBank Accession Number AJ508391

*Acetobacter xylinus*: lsxA GenBank Accession Number AB034152

*Gluconacetobacter diazotrophicus*: lsdA GenBank Accession Number L41732

In addition to the above-described methods, the gluX gene can also be inactivated by introducing a mutation into an expression control sequence which regulates the gluX gene, such as a promoter, Shine-Dalgarno (SD) sequence, operator, terminator, attenuator, or the like. An expression control sequence on a chromosome can be confirmed by the following methods: gene analysis software such as Genetix, expression analysis using a promoter probe vector, or on the basis of known information such as that obtained from Genbank or the like. The mutation which inactivates gluX is, for example, a mutation which replaces the promoter region of gluX with a weaker promoter, or a mutation which changes the promoter sequence as compared to a consensus sequence. These mutations can be introduced using a temperature-sensitive plasmid or a plasmid which is unable to replicate, as in the case mentioned above.

In addition to the aforementioned gene manipulation methods, examples of the method for inactivating gluX include, for example, treating a coryneform bacterium with ultraviolet irradiation or a mutagen used for typical mutagenesis such as N-methyl-N'-nitro-N-nitrosoguanidine (NTG) or nitrous acid, and selecting a strain in which gluX is inactivated. Moreover, inactivated gluX gene can also be obtained by artificially introducing a mutation into gluX by gene recombination based on error-prone PCR, DNA shuffling, or StEP-PCR (Firth A E, Patrick W M, Bioinformatics, 2005 Jun. 2, Statistics of protein library construction)

<3> Production of L-Glutamic Acid Using Coryneform Bacterium

L-glutamic acid can be efficiently produced by culturing a coryneform bacterium obtained as described above in a medium to produce L-glutamic acid in the medium, and collecting L-glutamic acid from the medium.

In order to produce L-glutamic acid using the coryneform bacterium of the present invention, the culture may be performed by conventional methods using a typical medium that contains a carbon source, a nitrogen source, an inorganic salt, and optionally includes organic micronutrients such as amino acids and vitamins. Either a synthetic or a natural medium may be used. Any kinds of carbon and nitrogen sources may be used so long as they can be utilized by the strain being cultured.

Saccharides such as glucose, glycerol, fructose, sucrose, maltose, mannose, galactose, starch hydrolysate, molasses, and so forth may be used as the carbon source. In addition, organic acids such as acetic acid and citric acid, and alcohols such as ethanol may also be used alone or in combination with other carbon sources.

Ammonia, ammonium salts such as ammonium sulfate, ammonium carbonate, ammonium chloride, ammonium phosphate, and ammonium acetate, nitrates, and so forth may be used as the nitrogen source.

Amino acids, vitamins, fatty acids, nucleic acids, and peptone, casamino acid, yeast extract, and soybean protein decomposition products which contain these substances may be used as the organic micronutrients. When an auxotrophic mutant strain that requires an amino acid etc. for growth is used, such a required nutrient is preferably added.

Phosphates, magnesium salts, calcium salts, iron salts, manganese salts, and so forth can be used as inorganic salts. Aerobic culturing is performed by controlling the fermentation temperature to 20 to 45° C. and adjusting the pH of the culture medium to 5 to 9. When the pH decreases during the culture, the medium is neutralized by adding alkali such as calcium carbonate or ammonia gas. Culture for about 10 to about 120 hours results in accumulation of a marked amount of L-glutamic acid in the medium, which is produced via a biosynthesis pathway which utilizes pyruvic acid as an intermediate.

When the chosen coryneform bacterium produces L-glutamic acid under certain various conditions, such as when biotin is restricted, and/or surfactants and/or penicillin are added, the medium is preferably adjusted to induce production of L-glutamic acid by the chosen bacterium. The concentration of the above substances in the medium is as follows. The concentration of biotin is less than 30 μg/L, preferably less than 20 μg/L, more preferably less than 10 μg/L, and the medium may not contain biotin at all. The concentration of penicillin in the medium is not less than 0.1 U/ml, preferably not less than 0.2 U/ml, and more preferably not less than 0.4 U/ml. The concentration of surfactants in the medium is not less than 0.5 g/L, preferably not less than 1 g/L, and more preferably not less than 2 g/L. However, any concentration of these substances can be used as long as L-glutamic acid production is induced. When antibiotic or surfactant is added to the medium, it is preferable that the medium contains a sufficient amount of biotin. In such a case, it is preferable that the medium contains more than 50 μg/L, preferably more than 100 μg/L, and more preferably more than 200 μg/L of biotin.

Furthermore, L-glutamic acid can be induced to precipitate into the medium by adjusting the medium conditions. Examples of such conditions include pH 5.0 to 4.0, preferably pH 4.5 to 4.0, more preferably pH 4.3 to 4.0, particularly preferably pH 4.0.

L-glutamic acid may be collected from the medium after the culture by a known method. For example, cells can be removed from the medium, and crystallization can be induced by concentration, ion exchange chromatography, or the like. When the culture is performed under conditions which induce precipitation of L-glutamic acid, the L-glutamic acid may be collected from the medium by centrifugation or filtration. L-glutamic acid which is dissolved in the medium may be precipitated and then separated.

EXAMPLES

Hereinafter, the present invention will be specifically explained with reference to the following non-limiting Examples.

Example 1

Construction of a Vector for Disrupting the sacB Gene (A) Construction of pBS3

The sacB gene (SEQ ID NO: 7) was obtained by PCR using the chromosomal DNA of *Bacillus subtilis* as a template and the oligonucleotides of SEQ ID NOS: 1 and 2 as primers. PCR was performed using LA Taq (TaKaRa) by incubating at 94° C. for 5 minutes and a cycle of denaturation at 94° C. for 30 seconds, annealing at 49° C. for 30 seconds, and extension at 72° C. for 2 minutes, which was repeated 25 times. The PCR product was purified in a conventional manner, and then blunt-ended by digestion with BglII and BamHI. This fragment was inserted into pHSG299 which had been cleaved with AvaII and blunt-ended. Using this DNA, competent cells of *Escherichia coli* JM109 (Takara Bio Inc.) were transformed, and the cells were applied to LB medium containing 25 μg/ml of kanamycin (henceforth abbreviated as Km), and cultured overnight. Then, the colonies that appeared were collected, and the individual single colonies were separated to obtain transformants. Plasmids were extracted from the transformants, and a plasmid in which the objective PCR product was inserted was designated pBS3. The construction scheme of pBS3 is shown in FIG. 1.

(B) Construction of pBS4S

Since a recognition site of the restriction enzyme SmaI is present in the kanamycin resistance gene on pBS3, a plasmid carrying a kanamycin resistance gene with the SmaI site disrupted by a silent nucleotide substitution (no change in the encoded amino acid) was obtained by crossover PCR. First, PCR is performed using pBS3 as a template and the synthetic DNAs of SEQ ID NOS: 3 and 4 as primers to obtain the amplification product of the N-terminal sequence of the kanamycin resistance gene. Furthermore, in order to obtain the amplification product of the C-terminal sequence of the Km resistance gene, PCR was performed using pBS3 as a template and the synthetic DNAs of SEQ ID NOS: 5 and 6 as primers. The objective PCR product was obtained by performing PCR using Pyrobest DNA Polymerase (Takara Bio Inc.) by incubating at 98° C. for 5 minutes and a cycle of denaturation at 98° C. for 10 seconds, annealing at 57° C. for 30 seconds, and extension at 72° C. for 1 minute, which was repeated 25 times. The sequences of SEQ ID NOS: 4 and 5 are partially complementary to each other, and the SmaI site which had been present in these sequences was disrupted by a silent nucleotide substitution. Then, in order to obtain a mutant kanamycin resistance gene fragment having a disrupted SmaI site, the aforementioned gene products of the N-terminus and C-terminus sequences of the kanamycin resistance gene were mixed in substantially equivalent molar amounts, and PCR was performed using this mixture as a template and the synthetic DNAs of SEQ ID NOS: 3 and 6 as primers to obtain an amplification product of the mutated Km resistance gene. The PCR product was obtained by performing PCR using Pyrobest DNA Polymerase (Takara Bio Inc.) by incubating at 98° C. for 5 minutes and a cycle of denaturation at 98° C. for 10 seconds, annealing at 57° C. for 30 seconds, and extension at 72° C. for 1.5 minutes, which was repeated 25 times.

Figure 2:
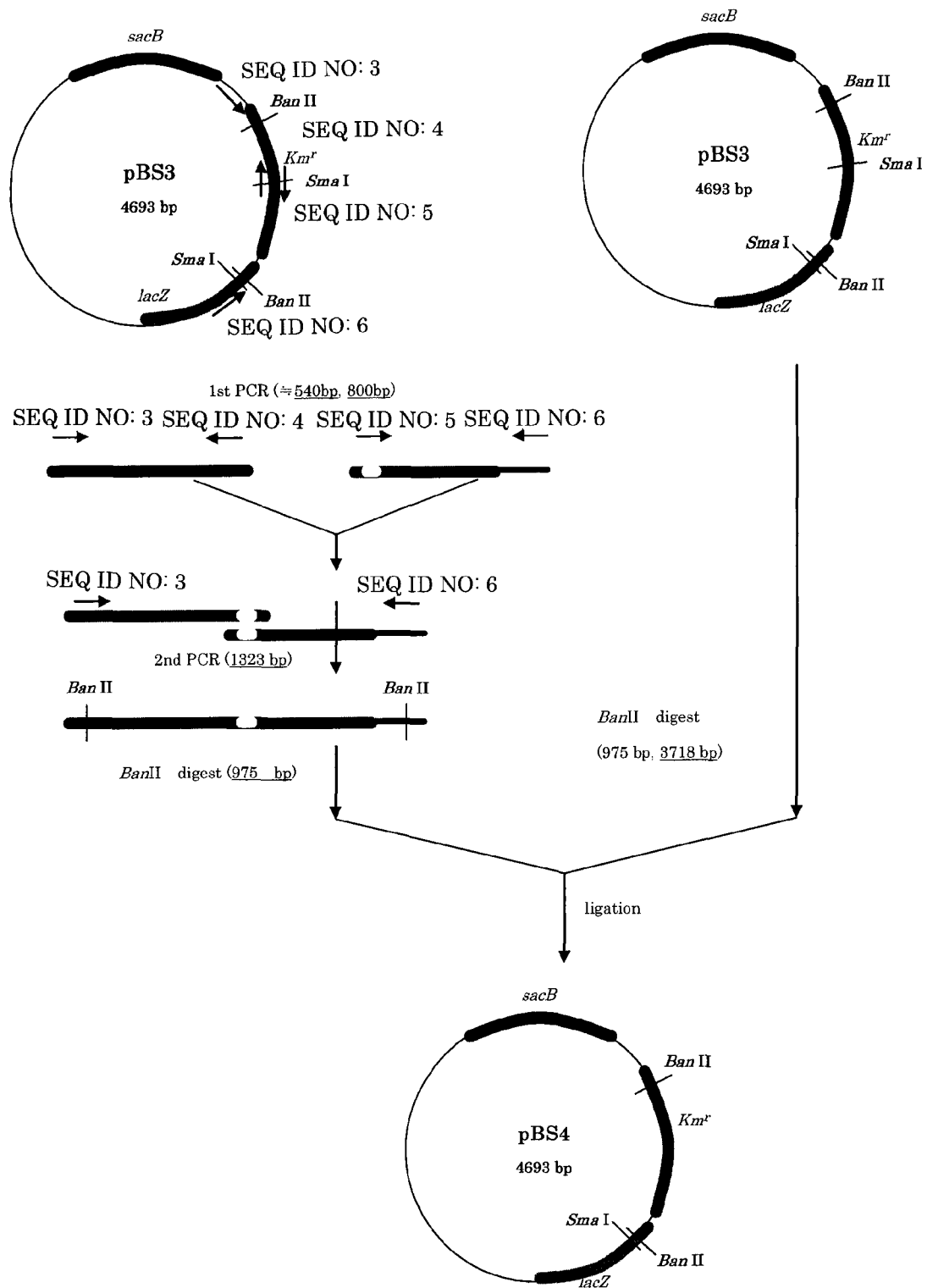
FIG. 2 shows the construction of the plasmid pBS4S.

The PCR product was purified in a conventional manner, then digested with BanII, and inserted into the BanII site of the pBS3 described above. Competent cells of *Escherichia coli* JM109 (Takara Bio Inc.) were transformed with the DNA, and the cells were applied to LB medium containing 25 µg/ml of kanamycin, and cultured overnight. Then, single colonies were separated from the colonies which appeared to obtain transformants. Plasmids were extracted from the obtained transformants, and a plasmid in which the objective PCR product was inserted was designated pBS4S. The construction scheme of pBS4S is shown in FIG. 2.

Example 2

Preparation of gluX-Deficient Strain of *C. glutamicum* ATCC 13869

Figure 3:
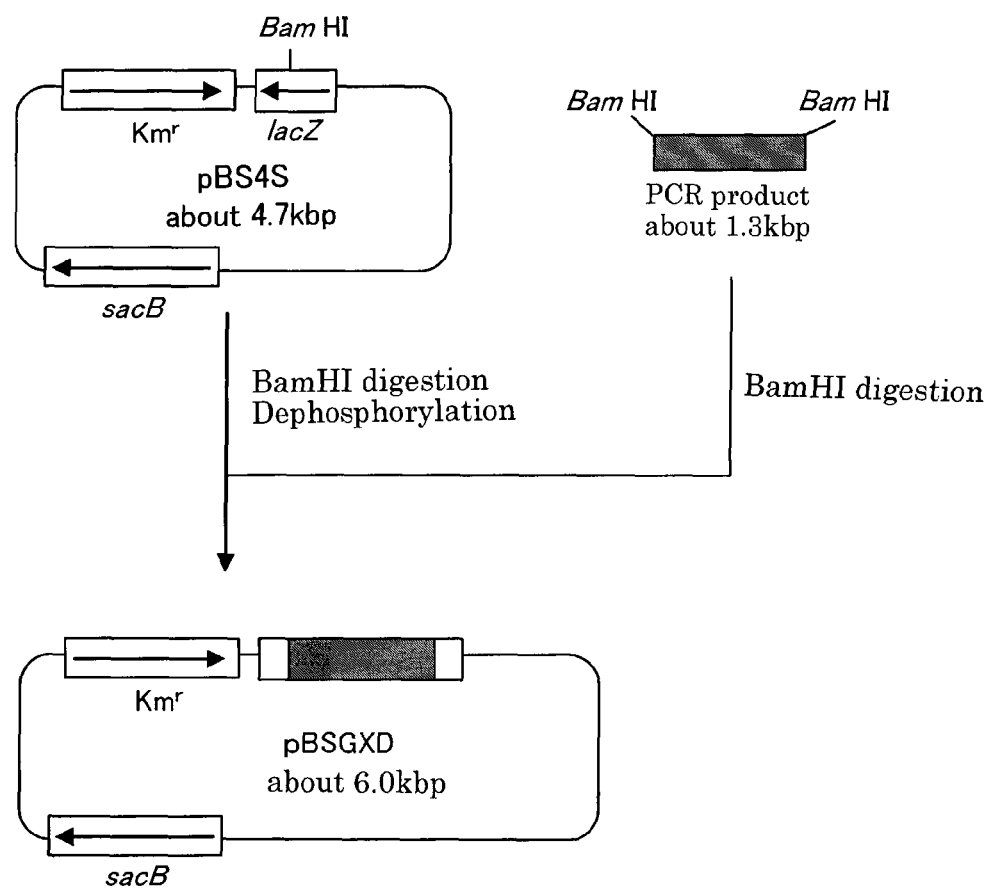
FIG. 3 shows the construction of the plasmid pBXGXD for disruption of gluX.

A plasmid for deleting the gluX gene was prepared. The chromosome was extracted from *C. glutamicum* ATCC 13869 using Bacterial Genomic DNA Purif. Kit (MS Techno Systems), and PCR was performed using this chromosome as a template and a combination of the primers of SEQ ID NOS: 9 and 10, and a combination of the primers of SEQ ID NOS: 11 and 12 to amplify fragments of about 650 bp, respectively. PCR was performed using Ex Taq (Takara Bio Inc.) with a cycle of denaturation at 94° C. for 30 seconds, annealing at 55° C. for 10 seconds, and extension at 72° C. for 1 minute, which was repeated 25 times. The primers of SEQ ID NOS: 9 and 10 were designed to amplify the region of the nucleotide numbers 401 to 1040 of SEQ ID NO: 16, and the primers of SEQ ID NOS: 11 and 12 were designed to amplify the region of the nucleotide numbers 1241 to 1920 of SEQ ID NO: 16. Then, PCR was performed using a solution prepared by mixing these two fragments as templates and the primers SEQ ID NOS: 13 and 14 to amplify a fragment of about 1.3 kb. PCR was performed using Ex Taq (Takara Bio Inc.) with a cycle of denaturation at 94° C. for 30 seconds, annealing at 55° C. for 10 seconds, and extension at 72° C. for 1.5 minutes, which was repeated 25 times. The primers of SEQ ID NOS: 13 and 14 were designed to add a BamHI sequence to the 5' end, and amplify the region of the nucleotide numbers 441 to 1870 of SEQ ID NO: 16 (including deletion of the region of nucleotide numbers 1041 to 1240). The amplified fragment was completely digested with BamHI, and ligated to the pBS4S vector described in Example 1 which had been similarly completely digested with BamHI (Ligation Kit Ver. 2 (Takara Bio Inc.) was used) to construct a vector for gluX disruption, pBSGXD. The construction scheme is shown in FIG. 3.

pBSGXD was introduced into *C. glutamicum* ATCC 13869 by the electric pulse method (Japanese Patent Laid-open No. 2-207791), and the cells were applied to the CM-Dex agar medium (5 g/l of glucose, 10 g/l of polypeptone, 10 g/l of yeast extract, 1 g/l of $KH_2PO_4$, 0.4 g/l of $MgSO_4.7H_2O$, 0.01 g/l of $FeSO_4.7H_2O$, 0.01 g/l of $MnSO_4.4-5H_2O$, 3 g/l of urea, 1.2 g/l of soy bean protein hydrolysate, 20 g/l of agar, adjusted to pH 7.5 with NaOH) containing 25 µg/ml of kanamycin. Culture was performed at 31.5° C., and then it was confirmed by PCR that the strain was a one time-recombinant strain in which pBSGXD was incorporated into the chromosome by homologous recombination. Whether a candidate strain is a one time-recombinant strain can be easily confirmed by performing PCR using the chromosome of the strain as a template, a specific sequence on pBS4S (SEQ ID NO: 15) and a sequence on the chromosome (SEQ ID NO: 9) as primers. Since the sequence of pBS4S is not present on the chromosome of a non-recombinant strain, any fragment amplified by PCR does not appear in the non-recombinant strain, and therefore discrimination is possible.

The obtained once-recombinant strain was cultured at 31.5° C. for one whole day in the CM-Dex liquid medium containing 25 µg/ml of kanamycin, and this medium was appropriately diluted, and applied to S10 plates (having a composition of the CM-Dex medium mentioned above in which 5 g/l of glucose was replaced with 100 g/l of sucrose). Several strains grown on the S10 plates and showing kanamycin sensitivity were selected, and PCR was performed using the chromosomes of these strains as templates and the sequences of SEQ ID NOS: 13 and 14 as primers to confirm that one strain among them was an objective gluX deficient strain. Since the region of nucleotide numbers 1041 to 1240 is deleted in the deficient strain, the amplified fragment is shorter than that of the non-deficient strain, and therefore discrimination is possible. The deficient strain obtained as described was designated ATCC 13869 ΔgluX.

Example 3

Measurement of the Produced Glutamic Acid by the ATCC13869ΔgluX Strain

The ability of the ATCC13869ΔgluX strain to produce glutamic acid was examined by culturing in a Sakaguchi flask. The ATCC 13869 and ATCC13869ΔgluX strains were cultured at 31.5° C. on the CM-2B agar medium (10 g/l of polypeptone, 5 g/l of yeast extract, 5 g/l of NaCl, 10 µg/l of biotin, 20 g/l of agar, adjusted to pH 7.0 with KOH) for one whole day, and inoculated into 20 ml of a seed culture medium (50 g/l of glucose, 30 g/l of ammonium sulfate, 1 g/l of $KH_2PO_4$, 0.4 g/l of $MgSO_4.7H_2O$, 0.01 g/l of $FeSO_4.7H_2O$, 0.01 g/l of $MnSO_4.4-5H_2O$, 200 µg/l of vitamin B1, 0.48 g/l of soy bean protein hydrolysate, 300 µg/l of biotin, adjusted to pH 8.0 with KOH). 1 g of calcium carbonate which had been previously sterilized by dry heat was added to the medium, and then culture was performed at 31.5° C. with shaking at a velocity of 115 rpm. After confirming that the total sugar was completely consumed, 1 ml of the seed culture medium was inoculated into 20 ml of a main culture medium (50 g/l of glucose, 30 g/l of ammonium sulfate, 1 g/l of $KH_2PO_4$, 0.4 g/l of $MgSO_4.7H_2O$, 0.01 g/l of $FeSO_4.7H_2O$, 0.01 g/l of $MnSO_4.4-5H_2O$, 200 µg/l of vitamin B1, 0.48 g/l of soy bean protein hydrolysate, 300 µg/l of biotin, adjusted to pH 8.0 with KOH), followed by adding 1 g of calcium carbonate which had been previously sterilized by dry heat, and then culture was performed at 31.5° C. with shaking at a velocity of 115 rpm. After 2.5 hours from the start of the culture, 4 g/l of Tween 40 (Sigma) was added. The amounts of the cells (absorption was measured at 620 nm), the produced glutamic acid, and the remaining saccharide after 17.5 hours are shown in Table 3.

It was confirmed that the production of glutamic acid by the ATCC13869ΔgluX strain increased as compared to that of the ATCC13869 strain, and thus confirming that deletion of the gluX gene was effective for improving glutamic acid production.

TABLE 1

|  | OD 620 nm | Glutamic acid (g/l) | Remaining saccharide (g/l) |
|---|---|---|---|
| ATCC13869 | 44.88 ± 0.77 | 21.5 ± 0.4 | 0.0 |
| ATCC13869ΔgluX | 43.81 ± 0.46 | 23.3 ± 0.1 | 0.0 |

INDUSTRIAL APPLICABILITY

According to the present invention, the fermentation yield of L-glutamic acid can be increased in a method for producing L-glutamic acid using a coryneform bacterium. Moreover, the present invention can be used for breeding of L-glutamic acid producing bacteria.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

The invention claimed is:

1. A method for producing an increased amount of L-glutamic acid as compared to the method using an unmodified *Corynebacterium glutamicum*, the method comprising
   A) culturing a modified *Corynebacterium glutamicum* in a medium, and
   B) collecting L-glutamic acid from the medium;
wherein said *Corynebacterium glutamicum* is modified by decreasing expression of a gluX gene as compared to an unmodified *Corynebacterium glutamicum* by a method selected from the group consisting of:
   (i) introducing a mutation into said gluX gene, and
   (ii) disrupting said gluX gene, or an expression control region thereof, on the *Corynebacterium glutamicum* chromosome;
wherein said gluX gene encodes a protein selected from the group consisting of:
   (a) a protein comprising the amino acid sequence of SEQ ID NO: 17, and
   (b) a protein which is encoded by a nucleotide sequence which hybridizes with the nucleotide sequence of 1001 to 1279 of SEQ ID NO: 16 under stringent conditions comprising washing at 0.1×SSC, 0.1% SDS at 60° C.

2. The method according to claim 1, wherein the gluX gene encodes a protein comprising the amino acid sequence of SEQ ID NO: 17.

3. The method according to claim 1, wherein the gluX gene comprises a DNA sequence comprising nucleotides 1001 to 1279 of SEQ ID NO: 16.

* * * * *

```
SEQUENCE LISTING

<160> NUMBER OF SEQ ID NOS: 17

<210> SEQ ID NO 1
<211> LENGTH: 24
<212> TYPE: DNA
<213> ORGANISM: Artificial
<220> FEATURE:
<223> OTHER INFORMATION: sacB primer 1

<400> SEQUENCE: 1
cgggatcctt tttaacccat caca                                              24

<210> SEQ ID NO 2
<211> LENGTH: 29
<212> TYPE: DNA
<213> ORGANISM: Artificial
<220> FEATURE:
<223> OTHER INFORMATION: sacB primer 2

<400> SEQUENCE: 2
gaagatcttc aaaaggttag gaatacggt                                         29

<210> SEQ ID NO 3
<211> LENGTH: 23
<212> TYPE: DNA
<213> ORGANISM: Artificial
<220> FEATURE:
<223> OTHER INFORMATION: sacB primer 3

<400> SEQUENCE: 3
ccttttgaag atcgaccagt tgg                                               23

<210> SEQ ID NO 4
<211> LENGTH: 44
<212> TYPE: DNA
<213> ORGANISM: Artificial
<220> FEATURE:
<223> OTHER INFORMATION: sacB primer 4

<400> SEQUENCE: 4
tacctggaat gctgttttcc cagggatcgc agtggtgagt aacc                        44

<210> SEQ ID NO 5
<211> LENGTH: 28
<212> TYPE: DNA
<213> ORGANISM: Artificial
<220> FEATURE:
<223> OTHER INFORMATION: sacB primer 5

<400> SEQUENCE: 5
cctgggaaaa cagcattcca ggtattag                                          28

<210> SEQ ID NO 6
<211> LENGTH: 23
<212> TYPE: DNA
<213> ORGANISM: Artificial
<220> FEATURE:
<223> OTHER INFORMATION: sacB primer 6
```

<400> SEQUENCE: 6
tgcaggtcga ctctagagga tcc                                                  23

<210> SEQ ID NO 7
<211> LENGTH: 2014
<212> TYPE: DNA
<213> ORGANISM: Bacillus subtilis
<220> FEATURE:
<221> NAME/KEY: CDS
<222> LOCATION: (464)..(1885)
<223> OTHER INFORMATION: sacB

<400> SEQUENCE: 7
gatccttttt aacccatcac atatacctgc cgttcactat tatttagtga aatgagatat         60
tatgatattt tctgaattgt gattaaaaag gcaactttat gcccatgcaa cagaaactat        120
aaaaaataca gagaatgaaa agaaacagat agattttttta gttctttagg cccgtagtct       180
gcaaatcctt ttatgatttt ctatcaaaca aagaggaaaa atagaccagt tgcaatccaa        240
acgagagtct aatagaatga ggtcgaaaag taaatcgcgc gggtttgtta ctgataaagc        300
aggcaagacc taaaatgtgt aaagggcaaa gtgtatactt tggcgtcacc ccttacatat       360
tttaggtctt ttttttattgt gcgtaactaa cttgccatct tcaaacagga gggctggaag      420
aagcagaccg ctaacacagt acataaaaaa ggagacatga acg atg aac atc aaa          475
                                              Met Asn Ile Lys
                                                1 aag ttt gca aaa caa gca aca gta tta acc ttt act acc gca ctg ctg          523
Lys Phe Ala Lys Gln Ala Thr Val Leu Thr Phe Thr Thr Ala Leu Leu
  5                  10                  15                  20 gca gga ggc gca act caa gcg ttt gcg aaa gaa acg aac caa aag cca          571
Ala Gly Gly Ala Thr Gln Ala Phe Ala Lys Glu Thr Asn Gln Lys Pro
                 25                  30                  35 tat aag gaa aca tac ggc att tcc cat att aca cgc cat gat atg ctg          619
Tyr Lys Glu Thr Tyr Gly Ile Ser His Ile Thr Arg His Asp Met Leu
         40                  45                  50 caa atc cct gaa cag caa aaa aat gaa aaa tat caa gtt cct gaa ttc          667
Gln Ile Pro Glu Gln Gln Lys Asn Glu Lys Tyr Gln Val Pro Glu Phe
     55                  60                  65 gat tcg tcc aca att aaa aat atc tct tct gca aaa ggc ctg gac gtt          715
Asp Ser Ser Thr Ile Lys Asn Ile Ser Ser Ala Lys Gly Leu Asp Val
 70                  75                  80 tgg gac agc tgg cca tta caa aac gct gac ggc act gtc gca aac tat          763
Trp Asp Ser Trp Pro Leu Gln Asn Ala Asp Gly Thr Val Ala Asn Tyr
 85                  90                  95                 100 cac ggc tac cac atc gtc ttt gca tta gcc gga gat cct aaa aat gcg          811
His Gly Tyr His Ile Val Phe Ala Leu Ala Gly Asp Pro Lys Asn Ala
                105                 110                 115 gat gac aca tcg att tac atg ttc tat caa aaa gtc ggc gaa act tct          859
Asp Asp Thr Ser Ile Tyr Met Phe Tyr Gln Lys Val Gly Glu Thr Ser
        120                 125                 130 att gac agc tgg aaa aac gct ggc cgc gtc ttt aaa gac agc gac aaa          907
Ile Asp Ser Trp Lys Asn Ala Gly Arg Val Phe Lys Asp Ser Asp Lys
    135                 140                 145 ttc gat gca aat gat tct atc cta aaa gac caa aca caa gaa tgg tca          955
Phe Asp Ala Asn Asp Ser Ile Leu Lys Asp Gln Thr Gln Glu Trp Ser
150                 155                 160 ggt tca gcc aca ttt aca tct gac gga aaa atc cgt tta ttc tac act         1003
Gly Ser Ala Thr Phe Thr Ser Asp Gly Lys Ile Arg Leu Phe Tyr Thr
165                 170                 175                 180 gat ttc tcc ggt aaa cat tac ggc aaa caa aca ctg aca act gca caa         1051

```
Asp Phe Ser Gly Lys His Tyr Gly Lys Gln Thr Leu Thr Thr Ala Gln
                185                 190                 195
gtt aac gta tca gca tca gac agc tct ttg aac atc aac ggt gta gag     1099
Val Asn Val Ser Ala Ser Asp Ser Ser Leu Asn Ile Asn Gly Val Glu
                200                 205                 210
gat tat aaa tca atc ttt gac ggt gac gga aaa acg tat caa aat gta     1147
Asp Tyr Lys Ser Ile Phe Asp Gly Asp Gly Lys Thr Tyr Gln Asn Val
                215                 220                 225
cag cag ttc atc gat gaa ggc aac tac agc tca ggc gac aac cat acg     1195
Gln Gln Phe Ile Asp Glu Gly Asn Tyr Ser Ser Gly Asp Asn His Thr
        230                 235                 240
ctg aga gat cct cac tac gta gaa gat aaa ggc cac aaa tac tta gta     1243
Leu Arg Asp Pro His Tyr Val Glu Asp Lys Gly His Lys Tyr Leu Val
245                 250                 255                 260
ttt gaa gca aac act gga act gaa gat ggc tac caa ggc gaa gaa tct     1291
Phe Glu Ala Asn Thr Gly Thr Glu Asp Gly Tyr Gln Gly Glu Glu Ser
                265                 270                 275
tta ttt aac aaa gca tac tat ggc aaa agc aca tca ttc ttc cgt caa     1339
Leu Phe Asn Lys Ala Tyr Tyr Gly Lys Ser Thr Ser Phe Phe Arg Gln
                280                 285                 290
gaa agt caa aaa ctt ctg caa agc gat aaa aaa cgc acg gct gag tta     1387
Glu Ser Gln Lys Leu Leu Gln Ser Asp Lys Lys Arg Thr Ala Glu Leu
        295                 300                 305
gca aac ggc gct ctc ggt atg att gag cta aac gat gat tac aca ctg     1435
Ala Asn Gly Ala Leu Gly Met Ile Glu Leu Asn Asp Asp Tyr Thr Leu
    310                 315                 320
aaa aaa gtg atg aaa ccg ctg att gca tct aac aca gta aca gat gaa     1483
Lys Lys Val Met Lys Pro Leu Ile Ala Ser Asn Thr Val Thr Asp Glu
325                 330                 335                 340
att gaa cgc gcg aac gtc ttt aaa atg aac ggc aaa tgg tac ctg ttc     1531
Ile Glu Arg Ala Asn Val Phe Lys Met Asn Gly Lys Trp Tyr Leu Phe
                345                 350                 355
act gac tcc cgc gga tca aaa atg acg att gac ggc att acg tct aac     1579
Thr Asp Ser Arg Gly Ser Lys Met Thr Ile Asp Gly Ile Thr Ser Asn
                360                 365                 370
gat att tac atg ctt ggt tat gtt tct aat tct tta act ggc cca tac     1627
Asp Ile Tyr Met Leu Gly Tyr Val Ser Asn Ser Leu Thr Gly Pro Tyr
        375                 380                 385
aag ccg ctg aac aaa act ggc ctt gtg tta aaa atg gat ctt gat cct     1675
Lys Pro Leu Asn Lys Thr Gly Leu Val Leu Lys Met Asp Leu Asp Pro
        390                 395                 400
aac gat gta acc ttt act tac tca cac ttc gct gta cct caa gcg aaa     1723
Asn Asp Val Thr Phe Thr Tyr Ser His Phe Ala Val Pro Gln Ala Lys
405                 410                 415                 420
gga aac aat gtc gtg att aca agc tat atg aca aac aga gga ttc tac     1771
Gly Asn Asn Val Val Ile Thr Ser Tyr Met Thr Asn Arg Gly Phe Tyr
                425                 430                 435
gca gac aaa caa tca acg ttt gcg cca agc ttc ctg ctg aac atc aaa     1819
Ala Asp Lys Gln Ser Thr Phe Ala Pro Ser Phe Leu Leu Asn Ile Lys
                440                 445                 450
ggc aag aaa aca tct gtt gtc aaa gac agc atc ctt gaa caa gga caa     1867
Gly Lys Lys Thr Ser Val Val Lys Asp Ser Ile Leu Glu Gln Gly Gln
        455                 460                 465
tta aca gtt aac aaa taa aaacgcaaaa gaaaatgccg atatcctatt           1915
Leu Thr Val Asn Lys
        470 ggcattttct tttatttctt atcaacataa aggtgaatcc catatgaact atataaaagc   1975 aggcaaatgg ctaaccgtat tcctaacctt ttgaagatc                          2014
```

<210> SEQ ID NO 8
<211> LENGTH: 473
<212> TYPE: PRT
<213> ORGANISM: Bacillus subtilis

<400> SEQUENCE: 8

```
Met Asn Ile Lys Lys Phe Ala Lys Gln Ala Thr Val Leu Thr Phe Thr
  1               5                  10                  15

Thr Ala Leu Leu Ala Gly Gly Ala Thr Gln Ala Phe Ala Lys Glu Thr
             20                  25                  30

Asn Gln Lys Pro Tyr Lys Glu Thr Tyr Gly Ile Ser His Ile Thr Arg
         35                  40                  45

His Asp Met Leu Gln Ile Pro Glu Gln Gln Lys Asn Glu Lys Tyr Gln
     50                  55                  60

Val Pro Glu Phe Asp Ser Ser Thr Ile Lys Asn Ile Ser Ser Ala Lys
 65                  70                  75                  80

Gly Leu Asp Val Trp Asp Ser Trp Pro Leu Gln Asn Ala Asp Gly Thr
                 85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
```

```
                385                 390                 395                 400
Asp Leu Asp Pro Asn Asp Val Thr Phe Thr Tyr Ser His Phe Ala Val
                    405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
                435                 440                 445

Leu Asn Ile Lys Gly Lys Lys Thr Ser Val Val Lys Asp Ser Ile Leu
            450                 455                 460

Glu Gln Gly Gln Leu Thr Val Asn Lys
465                 470

<210> SEQ ID NO 9
<211> LENGTH: 20
<212> TYPE: DNA
<213> ORGANISM: Artificial
<220> FEATURE:
<223> OTHER INFORMATION: gluX primer 1

<400> SEQUENCE: 9
ggcagcgatg aagcattgct                                                   20

<210> SEQ ID NO 10
<211> LENGTH: 40
<212> TYPE: DNA
<213> ORGANISM: Artificial
<220> FEATURE:
<223> OTHER INFORMATION: gluX primer 2

<400> SEQUENCE: 10
agggcaatga agtcaagcag ctggacggat cgtggagatc                             40

<210> SEQ ID NO 11
<211> LENGTH: 40
<212> TYPE: DNA
<213> ORGANISM: Artificial
<220> FEATURE:
<223> OTHER INFORMATION: gluX primer 3

<400> SEQUENCE: 11
gatctccacg atccgtccag ctgcttgact tcattgccct                             40

<210> SEQ ID NO 12
<211> LENGTH: 20
<212> TYPE: DNA
<213> ORGANISM: Artificial
<220> FEATURE:
<223> OTHER INFORMATION: gluX primer 4

<400> SEQUENCE: 12
ttccgtttgc gctggtgttg                                                   20

<210> SEQ ID NO 13
<211> LENGTH: 40
<212> TYPE: DNA
<213> ORGANISM: Artificial
<220> FEATURE:
<223> OTHER INFORMATION: gluX primer 5

<400> SEQUENCE: 13
gccgggatcc ttcccgctgc atccgcgagc tgtaccgcat                             40

<210> SEQ ID NO 14
<211> LENGTH: 40
```

```
<212> TYPE: DNA
<213> ORGANISM: Artificial
<220> FEATURE:
<223> OTHER INFORMATION: gluX primer 6

<400> SEQUENCE: 14
gccgggatcc ttatccacag acccagccgc tattcgacaa                    40

<210> SEQ ID NO 15
<211> LENGTH: 21
<212> TYPE: DNA
<213> ORGANISM: Artificial
<220> FEATURE:
<223> OTHER INFORMATION: gluX primer 7

<400> SEQUENCE: 15
gcttccggct cgtatgttgt g                                        21

<210> SEQ ID NO 16
<211> LENGTH: 2283
<212> TYPE: DNA
<213> ORGANISM: Corynebacterium glutamicum
<220> FEATURE:
<221> NAME/KEY: CDS
<222> LOCATION: (1001)..(1279)

<400> SEQUENCE: 16
gggtacttcg ccaggggtgg gggtgtattc cacacgagtt aacccaaggc gactttccgt   60
attcctattc accaccacgc cgatcttcca cagattgccc agcatttcta cggcacgctg  120
cgctttgccg ggtccggaaa actctttata tataaggttt ggttcggtga cagatccgag  180
acgcctgcgc cacatatcct gatttttcct gaaagtccgg ccacggcgt catcgcttcc   240 cggctccaca tcggtgtgct gataaaaaat ctcaatctca gggatagcga tcattagtgg  300
gtgcgcagtt tcagaaggct ggaacccaaa cgagcgccat tcagaatcgc tgcgcacatc  360
gagcttgcca atcaggctgg tcagcgcgtc aaaggtgtca ggcagcgatg aagcattgct  420
tgtcgacgca ccccccttgg ttcccgctgc atccgcgagc tgtaccgcat caagaagttg  480
gatagccaac gatgcacctt gtttggtggt caagttgggg agtgcacgta ctgtttccac  540
aatgaactgt tccacgcggc ttcgggctgc gggatcttgt tctttagaga tccgatcgat  600
ggttgtttcg aaatcattca tggccggccc ctgtccttct taagcttgtc tctggtttct  660
aagcataggc ataagcgcag ttcaataggg gaaatgacca ggaaacaagt tttattcaca  720
ccctgggggt gattctagtc actaagttta gctaaggtgt cctgagttgc ttttggggta  780
gcttaagtag ccttgacctg ctgttatgtt ttttgcggt ctggtataaa ttgtgccgat  840
ttaaggattt tgtggggggtg gattgaaatt agttggcccg atcccactac ttttcgcctg  900
gagtgcttgt aggttgatag aaagtaaact aaagtaaaca tcaggttaac agccggggt  960 tcaagtatta actccctcgg aaacagaaag gaacacgaca atg gct acc aca gct  1015
                                              Met Ala Thr Thr Ala
                                              1               5 tcc aag atc tcc acg atc cgt cca gca cag caa gat gct ctt tgg agc  1063
Ser Lys Ile Ser Thr Ile Arg Pro Ala Gln Gln Asp Ala Leu Trp Ser
            10                  15                  20 gta cgt gag gat ctt cac gct cgc ttc gat ggc ctg gtc gat cct gtc  1111
Val Arg Glu Asp Leu His Ala Arg Phe Asp Gly Leu Val Asp Pro Val
        25                  30                  35 cag gta gac gca att ttg gac cat gtc gca tct aac cgc gaa gcc aag  1159
Gln Val Asp Ala Ile Leu Asp His Val Ala Ser Asn Arg Glu Ala Lys
    40                  45                  50
```

```
atc acc gtc ttc agc aag att ttc atc gct cgc gag gca acc gct gca      1207
Ile Thr Val Phe Ser Lys Ile Phe Ile Ala Arg Glu Ala Thr Ala Ala
        55                  60                  65 ctt cag cag att gct ggc aac gtt aac gca gac ctg ctt gac ttc att      1255
Leu Gln Gln Ile Ala Gly Asn Val Asn Ala Asp Leu Leu Asp Phe Ile
 70                  75                  80                  85 gcc ctc aac cgt ggc atg gca gca taagttttag ctgcccataa attaactaaa     1309
Ala Leu Asn Arg Gly Met Ala Ala
                 90 ggccgggatt cactcgatgt gaatcccggc ctttagtttt tagtcttgtg ctcagagttt    1369 ccagatacag accaagcggc caataaagcc tattcggatt gtttcttagc cacctagttt    1429 ggctattacg ccttggacac caaactaggc agccgaagac ttcccgaaac tcacctcatc    1489 ggtcacatag gacggtcacg agggcactga gcaaacaaaa tagctgggat tcacatggtg    1549 tgaatcccag ccagtcgcta tttttaatc cttttcgcg tctacttcgc cttcttcggt     1609 cgattctggt gtccaaccat cggcccattt gccggtggtg aagtcataat caacatcatt    1669 gccttcttcg tcggtgcgct gataccagtc ggtgacgtga tcagcggtgg aatcgaaggt    1729 agcacccgct ccacgacctt cctctgcagg ttcgatggag agctcgaagt cgtcgccgtg    1789 ttcttccaag ccacgaacca ccgcgttaga gatggctgcc tttgcatagc gttgtcgaat    1849 agcggctggg tctgtggata aatccttaat aaaggcaata gccatcacga tcaacaccag    1909 cgcaaacgga atggcgatca aaatggtgag gttctgcaga ccagtcagcg cggattcgcc    1969 accagtaagc agcatgacca ccgcgatgcc catcatgcac agtccccaga acaccacgat    2029 caatttgttt ggtgcagggt taccttggga gctcatcgtt cccatcacca cggaggcgga    2089 atcggcagag gtaacaaaga atactgccag cacaaagatc aaaatgaacg tgtgatcga    2149 gtacagcgga aggttgctga acatatcaaa cagcacctgt tccttggatg aactgccgtc    2209 aaaaccatct acgttctcgc ggttcatcgt gatggcagtt ccaccgaaaa tggtgaacgc    2269 caggatcaaa atga                                                      2283
```

<210> SEQ ID NO 17
<211> LENGTH: 93
<212> TYPE: PRT
<213> ORGANISM: Corynebacterium glutamicum

<400> SEQUENCE: 17

Met Ala Thr Thr Ala Ser Lys Ile Ser Thr Ile Arg Pro Ala Gln Gln
1               5                   10                  15

Asp Ala Leu Trp Ser Val Arg Glu Asp Leu His Ala Arg Phe Asp Gly
            20                  25                  30

Leu Val Asp Pro Val Gln Val Asp Ala Ile Leu Asp His Val Ala Ser
        35                  40                  45

Asn Arg Glu Ala Lys Ile Thr Val Phe Ser Lys Ile Phe Ile Ala Arg
    50                  55                  60

Glu Ala Thr Ala Ala Leu Gln Gln Ile Ala Gly Asn Val Asn Ala Asp
65                  70                  75                  80

Leu Leu Asp Phe Ile Ala Leu Asn Arg Gly Met Ala Ala
                85                  90